(12) United States Patent
Arabi

(10) Patent No.: US 12,176,075 B1
(45) Date of Patent: Dec. 24, 2024

(54) METHOD OF MATCHING CONFORMERS OF DIFFERENT MOLECULES

(71) Applicant: UNITED ARAB EMIRATES UNIVERSITY, Al Ain (AE)

(72) Inventor: Alya A. Arabi, Al Ain (AE)

(73) Assignee: UNITED ARAB EMIRATES UNIVERSITY, Al Ain (AE)

( * ) Notice: Subject to any disclaimer, the term of this patent is extended or adjusted under 35 U.S.C. 154(b) by 0 days.

(21) Appl. No.: 18/389,392

(22) Filed: Nov. 14, 2023

(51) Int. Cl.
*G16C 20/30* (2019.01)
*G16C 20/10* (2019.01)
*G16C 20/62* (2019.01)

(52) U.S. Cl.
CPC ............ *G16C 20/30* (2019.02); *G16C 20/10* (2019.02); *G16C 20/62* (2019.02)

(58) Field of Classification Search
CPC ......... G16C 20/30; G16C 20/10; G16C 20/62
See application file for complete search history.

(56) References Cited

U.S. PATENT DOCUMENTS

| | | | |
|---|---|---|---|
| 7,014,795 B2 * | 3/2006 | Grigorov | H02N 11/006 977/762 |
| 7,523,026 B2 | 4/2009 | Tsuda et al. | |
| 7,904,283 B2 | 3/2011 | Merz, Jr. et al. | |
| 8,294,135 B2 * | 10/2012 | Lebedev | B82Y 10/00 977/752 |
| 10,626,154 B2 | 4/2020 | Steyart et al. | |
| 2005/0170385 A1 | 8/2005 | Carlson | |
| 2022/0068439 A1 | 3/2022 | Yamazaki et al. | |

FOREIGN PATENT DOCUMENTS

| | | | | |
|---|---|---|---|---|
| CN | 104093740 B | * | 1/2018 | ............... A61P 37/06 |
| WO | 2014033670 A2 | | 3/2014 | |

OTHER PUBLICATIONS https://blog.prepscholar.com/electronegativity-chart-trend-definition, 8 pages (Year: 2024).*
Chidangil et al., "A molecular electrostatic potential mapping study of some fluoroquinolone anti-bacterial agents," Molecular Modeling Annual, 4, Aug. 1998, 250-258.
Kahn, "Molecular Electron Density Surface," Department of Chemistry and Biochemistry, UC Santa Barbara, 2005-2012.
Ferro-Costas et al., "A QTAIM-based energy partitioning for understanding the physical origin of conformational preferences: application to the Z effect in O=C-X-R and related units," Journal of Computational Chemistry, vol. 33, Issue 32, Dec. 15, 2012.
Matta et al., "The bioisosteric similarity of the tetrazole and carboxylate anions: clues from the topologies of the electrostatic potential and of the electron density," European Journal of Medicinal Chemistry, vol. 45, Issue 5, May 2010, pp. 1868-1872.

(Continued)

*Primary Examiner* — Tung S Lau
(74) *Attorney, Agent, or Firm* — Nath, Goldberg & Meyer; Joshua B. Goldberg

(57) ABSTRACT

A system and method for matching conformers of different molecule are provided. The methods for matching conformers of different molecule include calculating average electron density (AED) values corresponding to a most electronegative group of the different molecules, and matching conformers of the different molecules based on a common AED.

10 Claims, 1 Drawing Sheet

(56) References Cited

OTHER PUBLICATIONS

Matta et al., "Electron Density Descriptors as Predictors in Quantitative Structure-to-Activity/Property-Relationships (QSAR/QSPR)," Future Medicinal Chemistry, vol. 3, No. 8, Jun. 27, 2011.
Arabi et al., "Electrostatic Potentials and Average Electron Densities of Bioisosteres in Methylsquarate and Acetic Acid," Future Medicinal Chemistry, vol. 8, No. 4, Mar. 15, 2016.
Arabi, "Route to Drug Design via Bioisosterism of Carboxyl and Sulfonamide Groups," Future Medicinal Chemistry, vol. 9, No. 18, Nov. 9, 2017.
Arabi, "Quantitative Evaluation of Bioisosteres in Drug Design," CBMC19 CompBioMed Conference 2019, Institute of Engineering and Technology, Savoy Place London, UK, Sep. 25-27, 2019.
Arabi, "Atomic and molecular properties of nonclassical bioisosteric replacements of the carboxylic acid group," Future Medicinal Chemistry, vol. 12, No. 12, May 13, 2020.
Faramarzi et al., "NBO and QTAIM Investigations of the conformers of 1, 4-dioxane-2, 3-bis(pyridin-1-ium) and 1, 4-dioxane-2, 5-bis(pyridin-1-ium) molecules," Eurasian Chemical Communications, (2020).
Setianto, et al., "Visualization the electrostatic potential energy map of graphene quantum dots," AIP Conference Proceedings, vol. 2219, No. 1, AIP Publishing LLC, Jan. 19, 2021.
Arabi, "Artificial Intelligence in Drug Design: Algorithms, Applications, Challenges and Ethics," Future Drug Discovery, vol. 3, No. 2, Apr. 29, 2021.
Duarte et al., "A New Synthetic Route and Comprehensive Topological Study of a Benzimidazole Derivative," Journal of the Brazilian Chemical Society, 33 (3), Mar. 2022.

\* cited by examiner

METHOD OF MATCHING CONFORMERS OF DIFFERENT MOLECULES

BACKGROUND

1. Field

The disclosure of the present patent application relates to methods and systems for matching conformers of different molecules to aid in many applications including but not limited to the development of drug design, to assist in determining chemical reactivities, to resolve materials science issues, or for other purposes.

2. Description of the Related Art

In general, various chemical and other physical properties of various molecules can be classified by numerous tools. For example, U.S. Pat. No. 10,626,154 discloses that x-ray crystallography can be used to generate a three-dimensional picture of the density of electrons within a molecule. This electron density can then be used to determine the mean positions of the atoms in the molecule, their chemical bonds, their disorder, and various other information.

Similarly, U.S. Pat. No. 7,904,283 discloses various computational methods for designing a drug by predicting free energy binding. Among the types of free energy binding used is entropic free energy, which comprises a conformational entropy component, calculated using a quantum mechanical Hamiltonian and/or a quantum mechanical/molecular mechanical approach.

Chemical conformers are chemical compounds that have the same molecular formula but a different rotation from one another at one or more bonds in the molecule. Chemical conformers are also known as conformational isomers.

However, there are no currently known tools capable of suitably analyzing and matching chemical conformers of different molecules. Currently, it is possible to look, e.g., at the energy levels of various conformers, yet it is not currently possible to transfer such knowledge to other molecules to aid in the development of new drug design, to assist in determining chemical reactivities, to resolve materials science issues, or for other purposes. Thus, a new tool solving these problems is desired.

SUMMARY

A system and method for matching conformers of different molecules are provided. The methods for matching conformers of different molecules include calculating average electron density (AED) values corresponding to a most electronegative group of the different molecules, and matching conformers of the different molecules based on a common AED.

The methods and systems described herein relate to the identification and matching of conformers of different molecules. More specifically, the present methods and systems relate to a new use of the Average Electron Density (AED) tool, a quantitative tool to assist in developing and classifying conformers of molecules of interest, and matching conformers of the different molecules based on a common AED. The present methods and systems can then be used to aid in the development of drug design and many other applications including, but not limited to, materials science applications, the development of chemical probes, determining chemical reactivities, conducting analyses of crystalline structures, synthesizing pairs of matching conformers, predicting matching conformers, creating new molecules with the desired property of the conformer, designing new molecules with conformer matching, developing a strategy of matching conformers of pairs to decide on their similarities in properties and reactivities (e.g. toxicity, polarizability) modelling conformers, and computational chemistry applications.

In one aspect, the present subject matter relates to a method for matching similar conformers of multiple molecules. In this regard, the present subject matter relates to methods for independently matching similar conformers of multiple molecules having a threshold difference of, in different embodiments, up to 1.5%, up to 1%, or up to 0.5%.

Accordingly, the method of matching conformers of each molecule can comprise: selecting each target molecule of interest; generating a list of conformers of the target molecule of interest; calculating average electron density (AED) values corresponding to a most electronegative group of the target molecule of interest; ranking the calculated AED values for conformers in each list; and matching conformers in the different list of conformers based on similarities in the calculated AED values.

In a further embodiment, the method of matching conformers among different molecule can comprise: selecting multiple target molecules of interest; generating a list of conformers of the multiple target molecules of interest; calculating average electron density (AED) values corresponding to a most electronegative group of one of the multiple target molecules of interest; and matching conformers in the list of conformers of the one of the multiple target molecule with conformers in the list of conformers of one or more other molecules of the target molecules of interest based on the percent difference in the AED values (e.g., 0.5%, 1%, and/or 1.5% difference). In this regard, a library of molecules can be selected for analysis in which a ranking of calculated AED values for each conformer of each molecule on the library of molecules can be generated and then compared to any one specific ranking of AED values for each conformer of a specific molecule to determine other molecules, and other conformers of such molecules, within the library of molecules that represent a match.

In another embodiment, the method for matching conformers of each molecule in the library of molecules being investigated, among multiple target molecules of interest, or the like can comprise: selecting a first target molecule of interest; generating a list of conformers of the first target molecule of interest; calculating average electron density (AED) values corresponding to a most electronegative group of the first target molecule of interest; ranking the calculated average electron density (AED) values for each conformer of the first target molecule of interest; and predicting matching conformers of the other molecules in the library of molecules being investigated, among the multiple target molecules of interest, or the like based on the molecules' respective calculated AED values. In an example, the match is proven and/or confirmed by inspecting the electrostatic potential (ESP) maps for each conformer of the various molecules being examined in the same receptor to facilitate a visual comparison of the electrostatic potential (ESP) maps while the receptor is kept constant. The matching conformers of the two molecules share similarities in the pose in the receptor, similarities in the topology of the electrostatic potential (ESP) maps, and possibly similarities in ranking according to docking scores. In an advantage, the conformers of the multiple molecules that share the same AED are likely to have a similar ESP map, and thus similar binding capabilities, similar reactivities, and therefore similar properties.

In a further embodiment, the presently claimed subject matter relates to a method for predicting shapes of electrostatic potential (ESP) maps for conformers of a second molecule based on AED similarities with a first molecule, the method comprising: selecting a first target molecule of interest; generating a list of conformers of the first target molecule of interest; calculating AED values for each of the conformers of the first target molecule of interest; generating ESP maps of each of the conformers of the first target molecule of interest; generating a list of conformers of a second molecule; calculating AED values for each of the conformers of the second molecule; matching conformers of the first target molecule of interest with conformers of the second molecule based on similarities in their respective AED values; and obtaining an electrostatic potential (ESP) map for the conformers of the second molecule matching the conformers of the first target molecule of interest, said ESP map of the conformers of the second molecule sharing similarities with the ESP map of the first target molecule of interest.

In certain embodiments, the calculated average electron densities (AED) values can be calculated as a sum of electron population divided by a sum of volumes, of all atoms.

In a further embodiment, the present subject matter relates to a method for identifying conformers of multiple molecules having desired material, chemical, pharmaceutical or other properties, the method comprising: identifying at least one conformer of one of the multiple molecules having the desired material, chemical, pharmaceutical, or other properties; selecting the identified at least one conformer of the one of the multiple molecules for further analysis; identifying any conformers of a remainder of the multiple molecules matching the identified at least one conformer of the one of the multiple molecules; and selecting the identified conformers of the remainder of the multiple molecules for further analysis. In an embodiment, these methods can further include synthesizing the identified conformers of the remainder of the multiple molecules to conduct the further analysis of the identified conformers of the remainder of the multiple molecules.

In one non-limiting example, the step of identifying the at least one conformer of one of the multiple molecules having the desired material, chemical, pharmaceutical or other properties comprises screening the conformers of the molecule for a desired shape. This desired shape permits the conformer of the molecule to bind to an active site of a receptor of interest or to react with other molecules. This is important as the shapes of different conformers can cause the various conformers to have different interactions with a given receptor e.g., a protein in drug design, and for some conformers to be able to bind to a receptor of interest, while others cannot. In this regard, the selection of conformers that react with a specific receptor structure can induce changes in the receptor structure, which can be linked with its active/inactive mode, or even with a potential modification of the receptor activity.

Likewise, different conformers of a molecule may have an impact on the chemical reactivities of the molecule, as depending on the ESP topology of a specific conformer, the molecule may be blocked from desired chemical reactions. Accordingly, studying the conformers of a molecule may help predict the reactivity of that molecule. Similarly, conformers of the molecules having the desired shape would be expected to share similar material properties.

In a next step, once the conformers of each molecule are determined, the conformers of pairs of molecules can be compared, one to the next, to find matching conformers. In an embodiment, the two molecules in the pair of molecules differ be a group having the same AEDs.

In this regard, the two molecules can have similar AEDs, one to the next, such that they are considered as "matching". Such AEDs of different molecules can be considered similar, or as matches to one another, if they have up to a 1.5% deviation from one another. In an additional embodiment, the AEDs of different molecules can be considered similar/matching if they have up to a 1% deviation from one another. In another embodiment, the AEDs of different molecules can be considered similar/matching if they have up to a 0.5% deviation from one another. However, particularly for those embodiments having a 1.5% or a 1% deviation from one another, depending on the size and complexity of the molecule, not every instance of AEDs having such similar values will be considered as perfect "matches"; rather, this "match" is a requirement of, but taken solely by itself is not dispositive of, matching conformers of different molecules. That is to say, all "matches" will have AED values within the designated percentage deviation from one another, but not all conformers within the designated percentage deviation are necessarily "matches".

The conformers of the pair of molecules can have similar reactivities with their receptors, with similar poses, ESP maps, and possibly rankings in their docking. Accordingly, this comparison and identification of matching conformers of the pair of molecules makes it possible to determine which conformers of the multiple molecules are likely to be a best fit for certain desired therapeutic effects.

In this regard, such methods may further comprise screening the conformers of the molecule for the desired chemical properties, pharmaceutical properties, or chemical and pharmaceutical properties. For example, in addition to the example of the different conformer shapes noted above, the desired pharmaceutical properties may be one or more selected from the group consisting of potency, solubility, permeability, metabolic stability, transporter effects, bioavailability, metabolism, clearance, and toxicity. Similarly, in addition to the example of the different conformer shapes noted above, the desired chemical properties may be one or more selected from of the group consisting of mechanical, electrical, thermal, magnetic, optical, and deteriorative properties which may impact surface chemistry as it relates to materials sciences, for example. Impacts on engineering applications are also possible, for the reasons given above.

These and other features of the present subject matter will become readily apparent upon further review of the following specification.

BRIEF DESCRIPTION OF THE DRAWINGS

FIG. 1A shows the ESP map for conformer 0 of molecule 1.

FIG. 1N shows the ESP map for conformer 6 of molecule 2.

DETAILED DESCRIPTION OF THE PREFERRED EMBODIMENTS

Figures 1A, 1B, 1C, 1D, 1E, 1F, 1G:
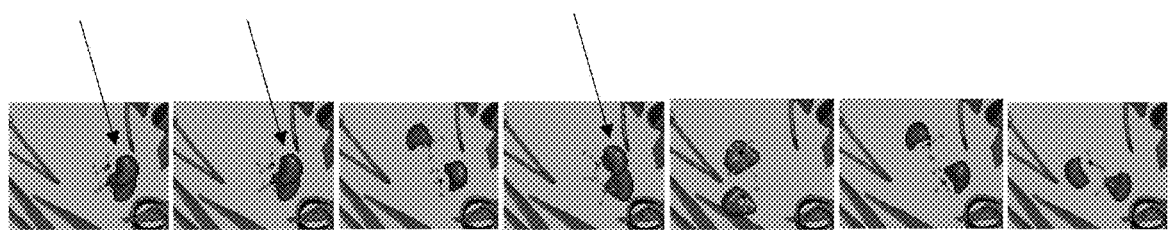
FIGS. 1A-1N shows exemplary ESP maps for conformers of the molecules 1 and 2 studied in the Examples herein, all conformers are in the same receptor captured at the same angle (to facilitate the comparison), as follows.
FIG. 1B shows the ESP map for conformer 1 of molecule 1.
FIG. 1C shows the ESP map for conformer 2 of molecule 1.
FIG. 1D shows the ESP map for conformer 3 of molecule 1.
FIG. 1E shows the ESP map for conformer 4 of molecule 1.
FIG. 1F shows the ESP map for conformer 5 of molecule 1.
FIG. 1G shows the ESP map for conformer 6 of molecule 1.

The presently described subject matter relate to the identification and matching of conformers of different molecules. More specifically, the present methods and systems relate to a new use of the Average Electron Density (AED) tool to assist in developing and matching conformers of different molecules. The activity of a molecule is linked to its chemical structure. Therefore, studying this structure is extremely important. Once the chemical conformers of a molecule are classified, they can be compared to the chemical conformers of different molecules based on a common AED. Further studies can be done to determine how the conformers of each molecule may impact drug design, chemical reactivities, engineering applications, and materials science applications, among others.

In one embodiment, the present subject matter relates to a method for independently ranking conformers of multiple molecules and comparing the AED values after these rankings to find matching conformers of different molecules, the method comprising: selecting a target molecule of interest; generating a list of conformers of the target molecule of interest; calculating average electron density (AED) values corresponding to a most electronegative group of the target molecule of interest; ranking the calculated AED values for each conformer; and classifying each conformer in the list of conformers based on the ranking of the calculated AED values.

Once ranked, it is then possible to select the conformer of a second molecule of interest which is most like to be capable of replacing the most desirable conformer of the target molecule of interest, depending on the specific use involved.

In this regard, in an embodiment, the AED values can be calculated for an active moiety of each molecule with respect to a particular desired activity, with such active moiety potentially capped with a methyl group. In the cases where such capping is present, the methyl capping group is excluded from the determination of the AED values.

This approach permits the translation of conformers to numbers using quantum methods. Previously, it was possible to evaluate and classify conformers based on, for example, their coordinates. The present tool represents a new highly accurate and specific quantitative method for evaluating, measuring, classifying, matching, and working with conformers.

List of Conformers

The list of conformers for a specific molecule can be generated using any specific software package known to one of ordinary skill in the art. By way of non-limiting example, the list of conformers for any molecule can be generated using Omega from the OpenEye Scientific software package, owned by Cadence Molecular Sciences (Santa Fe, NM).

Other alternative software packages are available as well for generating the list of conformers. One such alternative software package is the Spartan software, owned by Wavefunction, Inc. (Irvine, CA), or the open-source software tools RDKit, OpenBabel, or Avogadro. Any other suitable software package having such capabilities are further contemplated for use herein.

Quantum Mechanics (QM) Simulation

Once the list of conformers for a particular molecule has been generated, a quantum mechanics (QM) simulation can be performed on the various identified conformers.

In one embodiment, the quantum mechanics (QM) simulation can be performed using Gaussian® software, for example, Gaussian 16, available from Gaussian, Inc. (Wallingford, CT), which is an electronic-structure modeling software that facilitates quantum chemistry calculations. Other QM software, such as Q-Chem (available from Q-Chem, Inc., Pleasanton, CA), The General Atomic and Molecular Electronic Structure System (GAMESS, maintained by members of the Gordon Research Group at Iowa State University, Ames, IA), or MolPro (available from the University of Stuttgart, Stuttgart, Germany) could be used. This QM analysis will obtain a wavefunction file from which the various properties of each conformer can be extracted. Therefore, the Gaussian 16 software is capable of completing a quantum mechanics (QM) simulation for each conformer in the list of conformers, and generating the wavefunction from which volumes and electron densities will be extracted after the QTAIM analysis.

In drug design, for example, it is important to rationally design molecules with a good shape complementarity to the appropriate receptor. The shape of a molecule can be determined uniquely given the unique electron correlations and the Pauli exclusion principle which prohibits two electrons of any molecule to have the same four electronic quantum numbers.

Further, the quantum mechanics is a probabilistic theory, and the electron density falls off roughly exponentially with the distance from the nucleus, and the repulsive energy grows roughly exponentially as the distance between two nuclei decreases. In typical molecules, the increase is so rapid that one molecule cannot penetrate a region just about half an angstrom beyond the point of minimum interaction. The electron density depends on the atomic composition and the chemical connectivity of atoms in the molecule. One way to determine molecular shape is to calculate the electron density and display the region where the electron density is larger than some cut-off value as a three-dimensional surface. Such calculations necessitate a quantum chemical approach and are possible with any molecule.

Average Electron Density (AED)

The average electron density (AED) tool is based on the partitioning of a molecule into atomic basins using the quantum theory of atoms in molecules (QTAIM) partitioning scheme. The average electron density (AED) is defined as the total electron population of a group of a molecule or of the full molecule divided by the corresponding volume.

The internal interatomic limits between two atoms are determined by the internal zero-flux interatomic surfaces within the molecular interior, and the outer limit is set at the external 0.001 atomic unit isodensity envelope. The volumes and electron populations used to calculate the AED are those defined within Bader's quantum theory of atoms in molecules, a theory that partitions the molecular electron density into separate atomic basins separated by surfaces of zero-flux in the gradient vector field associated with the density. The atomic properties are then obtained by numerical integrations over each atomic basin. The AED properties of a specific molecular group are the sum of the properties of the atoms constituting this group.

The average electron density of a group is given by the formula:

$$\rho = \Sigma Ni / \Sigma Vi \tag{8}$$

where Ni is the electron population of each atom i, and Vi is the volume of each atom i.

In one embodiment, the wavefunction file obtained from the QM simulation can be further analyzed and processed using AIMAll software, from TK Gristmill Software (Overland Park, KS), based on the QTAIM theory. The AIMAll software package can be used for atomic integrations based on QTAIM. The interatomic basins can be delimited by zero-flux surfaces, and the outer limit of the atomic basins can be defined at three different isodensity envelopes of 0.0004, 0.001, and 0.002 a.u. AIMAll software is typically used for performing quantitative and visual QTAIM analyses of molecular systems, starting from molecular wavefunction data.

Likewise, AED values can be calculated by starting with, for example, a Gaussian software package, such as, for example, Gaussian16, with molecules optimized in the gas phase. In one embodiment, the level of theory used is the B3LYP density functional theory, namely B3LYP/6-311++ G(d.p)//B3LYP/6-311++ G(d.p) with ultrafine pruned (99, 590) grids and 'tight' self-consistent field optimization criteria. Here even if other (reasonable) details of the QM simulation are used, they will still give the same result.

In another embodiment, the Hershfield scheme may be used for partitioning the basins of atoms in molecules. The Hirshfeld (1977) method apportions the electron density among the atoms by the appropriate weighting. The weights are related by the atomic contribution to the promolecular density:

$$w_A(r) = \frac{\rho_{utm}^A(r)}{\rho_{pro}(r)}$$

The fragment of the density apportioned to atom A is $$\beta_{frag}^A(r) = w_A(r) \rho_{mol}(r)$$

An alternative scheme is based on the atomic contributions to the total promolecular potential $V_{pro}$ defined as the sum of the electronic and nuclear contributions.

In one embodiment of the present methods, AED values are determined for only a most electronegative group of the molecule being studied. In another embodiment, AED values are determined for the entire molecule being studied.

Once the AED values are generated and ranked, conformers can then be matched based on their AED values.

Accordingly, the AED tool represents a technological advancement for matching similar conformers of not just one molecule, but also of multiple molecules. The strength of the AED tool for matching conformers, namely that the AED is a quantum tool that accounts for a multitude of quantum properties rather than only classical properties, making it a lot more accurate.

Electrostatic Potential Maps (ESPs)

Molecular ESPs were first introduced in the 1970s, and they are ubiquitously used for the identification of electrophilic and nucleophilic sites for predicting reactivities and gaining more insight about the directions of interactions, and thus mechanisms of various processes. Molecular electrostatic potentials are typically calculated from a molecule's charge density (the continuous electron density and the discrete nuclear charge distribution) and can be used to identify the reactive regions of a molecule.

The molecular ESP, V(r), is obtained at the quantum level by the following formula:

$$V(r) = \sum_A \frac{Z(A)}{|R(A) - r|} - \int \frac{\rho(r')}{|r' - r|} dr' \tag{9}$$

where Z(A) is the atomic number, R(A) is the position vector of nucleus A, r is the position vector of the point at which V(r) is evaluated and ρ(r') is the electron density at a position vector r'. The results of the equation are in atomic units, with the electronic charge taken as unity.

Various software packages offer three ways to evaluate the electrostatic potential. First, the true electrostatic potential can be calculated based on molecular orbital data. This is rather time consuming, especially if large Gaussian basis sets were used to form molecular orbitals but should give the best representation of the electrostatic potential. Second, fitting of the electrostatic potential can be performed based on the quantum-chemically derived multipole moments of the molecule. In other words, the software tries to determine what kind of potential would best reproduce the dipole and octupole moment of the molecule. Third, the electrostatic potential can be calculated based on partial atomic charges.

ESP maps are typically limited to qualitative comparisons. However, by combining the similarities observed with AED to the similarities observed in ESP maps for conformers of different molecules, it is now possible to quantitatively determine similarities and differences between different conformers of different molecules. That is, the present subject matter is directed to use of the AED value of conformers of different molecules to predict the shapes of the electrostatic potential maps of conformers and find matching pairs of conformers. In one embodiment, the AED value of the most electronegative group of the molecule being studied is used to predict the shapes of the electrostatic potential maps of conformers of different molecules. That is, the AED value can be used herein to predict the ESP maps of various conformers of different molecules that share similar shapes and interactions.

ESP maps can be plotted using a variety of software packages presently available to those of ordinary skill in the art. By way of non-limiting example, the subunit Vida from the OpenEye Scientific software package, owned by Cadence Molecular Sciences (Santa Fe, NM), can be used to plot ESP maps of a given molecule. Vida is typically used for molecular modeling, as it can present advanced 3D graphics for high quality molecular visualizations. Similarly, the ChemCraft software package can likewise be used to generate ESP maps of a given molecule. ChemCraft is another graphical software package for visualization of quantum chemistry computations, particularly useful with Gaussian software, and is available at https://www.chemcraftprog.com. ChemCraft can render 3D pictures of molecules by atomic coordinates with the possibility to examine or modify any geometrical parameter in the molecule. ChemCraft can be used as a graphical user interface for the GAMESS (Gordon Research Group, Iowa State University) and Gaussian program packages, as can any other QM package.

Many other molecular visualization programs allow display of electrostatic potential maps based on quantum chemical calculations. MOLDEN (available at https://www.theochem.ru.nl/molden) can calculate electron density surfaces and electrostatic potential surfaces based on the information in the output files of Gaussian or Firefly (PC GAMESS) calculations.

To obtain ESP maps, the results of using the above equation on a specific molecule, conformer, etc. are used to generate a figure, or "map", showing the different lobes and features of the specific compound.

Drug Design

Once the present methods are performed to classify the specific conformers of a given molecule, the knowledge can be used to determine which conformers specifically would be best suited for drug design. This knowledge can then be extended to the conformers of other molecules matching the identified conformer of the first molecule identified as best suited for drug design. The selected matching conformer(s) can then be synthesized to conduct further analysis on their suitability for drug design.

Conformational changes in a drug molecule can have drastic effects on its efficacy. The changes in conformation can cause a change in the stability (and therefore the half-life) of the molecule, but more importantly they cause a change in the shape of the molecule (and therefore its spatial arrangement), which may block it sterically from binding into the active site of the relevant receptor. Accordingly, the present tool is extremely helpful for determining which conformers of various drug molecules are most likely to bind to the active site of the relevant receptor, thus speeding the drug design process by allowing the focus to be on those conformers most likely to be successful. This can improve lead optimization and drug design by optimizing pharmaceutical properties, improving potency, enhancing specificity, and reducing side effects, all of which can improve the wellbeing of patients, reduce their pain, reduce inconveniences of facing side effects, and save money for the pharmaceutical companies in developing new drugs.

The screening process to determine potential drug candidates can be conducted according to any method known to those of ordinary skill in the art such as, for example, using high-throughput screening arrays. The present methods and systems can speed up what is commonly a long and difficult process by targeting specific conformers of the selected molecules that are more likely to possess a desired activity, removing one or more steps from the typical screening process. The present methods and systems act as a filter to enrich the hit rate compared with typical random screening of conformers of a given molecule, but not different molecules, although the latter is also possible.

Further, the present methods can assist in rapidly identifying potential candidates for treating a specific disease, disorder, or condition. This can be particularly useful when there is an urgent need for treating such a disease, disorder, or condition, for example, when a new disease starts spreading among humans, thus requiring urgent new drugs for treatment. COVID-19 would be one non-limiting example in this regard.

In cancer treatment, for example, the efficacy of the methotrexate drug to inhibit dihydrofolate reductase (DHFR) is influenced by the rate of proton tunneling, which itself depends on the conformer of the molecule. The AED tool can differentiate between the conformers that could or could not have proton tunneling, both for the initial molecule of interest and the second molecule of interest, and synthesize ones that have the desired properties.

In another example, inhibition of bacterial RNAP with the Gfh1-CTD inhibitor is reported as anti-bacterial therapies. At different pH, different conformers of Gfh1-CTD are available. At lower pH, the formed conformer is active and good for treatment, and at higher pH the conformer formed is not active. The AED tool can distinguish all the conformers of Gfh1-CTD that can or cannot inhibit RNAP and synthesize the one that do inhibit. Such learnings can be extended to identify the conformer(s) of a second molecule of interest likely to have such similar properties.

In a further example, NMR spectroscopy sometimes identifies only certain potent conformers of a ligand (but not others) to act on the antibiotic target LpxC. The AED tool can group the conformers into the active vs. inactive ones for various molecules.

The inhibition of EphB4 is used to treat cancer (e.g., prostate cancer). Crystallographic studies of anilinopyrimidine inhibitors of EphB4 have highlighted two alternative conformers. The AD tool can differentiate which other conformers are likely to bind or not to this active site and, by extension, which conformers of a second molecule are more likely to bind to this active site.

Once the best conformer for the specific drug design is selected, this can then be translated to identifying the matching conformer of the other molecule which is also likely to be suitable for the drug design. Once either conformer is selected, the conformer can then be produced, synthesized, or the like to conduct further testing under real world conditions.

Materials Science

Once the present methods are performed to classify the specific conformers of a given molecule, the knowledge can be used to determine which conformers specifically would be best suited for satisfying certain materials science needs and requirements. This knowledge can then be extended to the conformers of other molecules matching the identified conformer of the first molecule identified as best suited for satisfying certain materials science needs and requirements. The selected matching conformer(s) can then be synthesized to conduct further analysis on their suitability for satisfying certain materials science needs and requirements under real world conditions.

For one example, selecting a building material based on different conformers of the same molecule can lead to different physical properties of the material build, e.g., due to possibly different electron conductivity (melting properties, etc.). Therefore, classifying conformers of a first molecule and finding matching conformers of other molecules means moving one step forward in grouping conformers that would likely share similar material properties once used in building materials. This can be seen from Blaskovits et al., "Is a Single Conformer Sufficient to Describe the Reorganization Energy of Amorphous Organic Transport Materials?," *J. Phys. Chem. C* 2021, 125, 31, 17355-17362 (https://pubs.acs.org/doi/10.1021/acs.jpcc.1c04067), the contents of which are hereby incorporated by reference in their entirety. In this way, both the initially selected conformer and the conformer of the matching molecule can be physically tested to ensure they share similar and desirable material properties, for example, when producing building materials.

In another, non-limiting example, the identification of the most active conformers of the different molecules can lead to the selection, testing, and use of a specific conformer of a particular molecule to maximize the molecule's change in state, malleability, color, resistance, permeability, degradability, breaking points, and the like to match a desired use for the molecule.

Chemical Reactivities

Once the present methods are performed to classify the specific conformers of a given molecule, the knowledge can be used to determine which conformers specifically would be best suited for various chemical reactivities. This knowledge can then be extended to the conformers of other molecules matching the identified conformer of the first molecule identified as best suited for various chemical reactivities. The selected matching conformer(s) can then be synthesized to conduct further analysis on their suitability for various chemical reactivities.

Conformational changes in a molecule can have drastic effects on its ability to react with other molecules. Different conformers have different shapes, i.e., their densities change. Thus, matching conformers of different molecules means classifying conformers in groups that share similar reactivities. Likewise, depending on the shape of the conformer, it may be sterically blocked from reacting with another molecule. Accordingly, the present tool is extremely helpful for determining which conformers of multiple molecules are most likely to successfully complete various chemical reactions. In this regard, both the initially selected conformer and the conformer of the matching molecule can be physically tested to ensure they share similar and desirable chemical reactivities under real world conditions.

Other Uses

Some of the other uses for the presently described tool include the following:
1. Help identify matching conformers of different molecules, and therefore synthesize new molecules, that can improve chemical processes (for example, assist in differentiating which catalyst is active or not to permit expediting reaction synthesis and industrial activities).
2. Differentiate which environmental molecules can be considered to be equally polluting based on their interactions with a given receptor, which can have implications on the wellbeing of humans and on saving our planet.
3. Guide decision makers in whether or not chemicals/drugs should be banned for the safety of the society, based on their AED similarities to conformers of other known harmful chemicals.
4. Help quality assurance teams by determining if conformers of different molecules may be toxic to the body or harmful to the environment, in which case their use should be rejected.
5. This tool has superiority in its competence of being widely applicable to endless applications in many industries with a robust performance (the tool can match conformers of different molecules with differences as small as 3%, 1%, 0.5%, and/or 0.05% in their AED values). It is thus a versatile tool which can be applicable/useful in ample industrial sectors.
6. Save many experimental tests and therefore save money, time, and the environment from experimenting on potentially harmful molecules.
7. Select those conformers of certain molecules most likely to be successfully applied in aromatherapy and/or in perfumeries. For example, different conformer of the same molecule can have different smells and different olfactory properties. The AED tool can be used to know which conformers have different smells, and to use it to synthesize conformers in aroma therapy and perfumeries. By way of non-limiting example, different conformers (chair and boat conformers) of a disubstituted cyclohexane generate cis and trans enantiomers can have different reactivities and properties, and different stabilities or energies, such as cis- and trans-1, 2-difluoroethenes, which have altering IR spectra, and thus different odorant vibrations.

EXAMPLES

Example 1—Procedure for Ranking the AEDs, Matching Conformers of Molecules, and Generating the ESP Maps (FIGS. 1A-1N) for Molecules 1 and 2

The following describes the methodology used for ranking the AEDs, matching conformers of different molecules, and generating the ESP maps for two different molecules to confirm the match between conformers of the two molecules, identified herein as molecules 1 and 2, and having the following respective structures:

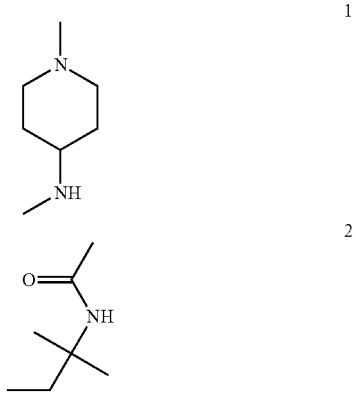

1. Conformers of molecules 1 and 2 were generated. A total of 7 conformers were generated for each of molecule 1 and molecule 2.
2. The xyz coordinates of each conformer of each molecules were extracted to build Gaussian input files.
3. Gaussian single point simulations were completed using the B3LYP functional with a triple zeta Pople basis set and ultrafine grids.
4. AIMAll analysis was completed on the wavefunction generated from the Gaussian simulations.
5. The volume (v) and electron population (e) in each atom of the most electronegative group was collected from the AIMAll output.
6. The AED was calculated for each conformer of each molecule. The AED values of all conformers of each molecule are ranked. Conformers of different molecules (molecule 1 and molecule 2 in this case) are matched based on a common AED value within 0.05% difference in this case. The matching groups of conformers now can share the same reactivity in chemistry, interaction in drug design, and/or properties in material sciences, etc.

Figures 1H, 1I, 1J, 1K, 1L, 1M, 1N:
FIG. 1H shows the ESP map for conformer 0 of molecule 2.
FIG. 1I shows the ESP map for conformer 1 of molecule 2.
FIG. 1J shows the ESP map for conformer 2 of molecule 2.
FIG. 1K shows the ESP map for conformer 3 of molecule 2.
FIG. 1L shows the ESP map for conformer 4 of molecule 2.
FIG. 1M shows the ESP map for conformer 5 of molecule 2.

7. Alternatively, the AED was calculated for each conformer of each molecule. The AED difference between each possible pair of conformers from molecule 1 and molecule 2 was calculated. Then the matching conformers were determined based on AED differences that did not exceed, in this case, 0.05%,
8. Conformers 0, 1, and 3 of molecule 1 were determined to match with conformers 4 and 6 of molecule 2. The matched conformers have the same docking pose with respect to one receptor, as illustrated in FIGS. 1A-1N (the arrows point at the similar pose of the negative lobes in the ESP maps), and as shown in the following Tables 1 and 2:

TABLE 1

Molecule 1

| AED Value | Conformer No. |
|---|---|
| 0.055124 | 4 |
| 0.055638 | 5 |
| 0.055725 | 2 |
| 0.055726 | 6 |
| 0.055835 | 0 |
| 0.055835 | 3 |
| 0.055835 | 1 |

TABLE 2

Molecule 2

| AED Value | Conformer No. |
|---|---|
| 0.055803 | 5 |
| 0.055811 | 6 |
| 0.055978 | 4 |
| 0.055989 | 1 |
| 0.055990 | 0 |
| 0.056001 | 3 |
| 0.056005 | 2 |

9. Select the conformers of the molecule 1 and molecule 2 having matching AED values, as BOLDED in Tables 1 and 2 above, and qualitatively sharing similar ESP maps, as seen in FIGS. 1A, 1B, and 1D for molecule 1 and FIGS. 1M and 1N for molecule 2, in such a way that they share any similarity in, e.g., structure or effects. As can be seen, those conformers having matching AED values also share matching poses in the receptor as seen in the displayed figures, which are not shared by those conformers which do not have matching AED values.

It is to be understood that the methods and systems described herein are not limited to the specific embodiments described above, but encompasses any and all embodiments within the scope of the generic language of the following claims enabled by the embodiments described herein, or otherwise shown in the drawings or described above in terms sufficient to enable one of ordinary skill in the art to make and use the claimed subject matter.

I claim:

1. A method for matching conformers of different molecules sharing desired chemical, material, or pharmaceutical properties, the method comprising:
   selecting a target molecule of interest;
   generating a list of conformers of the target molecule of interest;
   calculating, using an average electron density (AED) tool, average electron density (AED) values corresponding to a most electronegative group of the target molecule of interest;
   ranking the calculated average electron density (AED) values for each conformer of the target molecule of interest;
   identifying and grouping each conformer in the list of conformers based on the ranking of the calculated average electron density (AED) values for each conformer of the target molecule of interest;
   identifying at least one conformer of the target molecule of interest by screening the conformers of the target molecule of interest for a desired shape permitting the identified conformers to have a desired interaction with a given protein or receptor;
   selecting a second molecule of interest;
   generating a list of conformers of the second molecule of interest;
   calculating, using the AED tool, average electron density (AED) values corresponding to a most electronegative group of the second molecule of interest;
   ranking the calculated average electron density (AED) values for each conformer of the second molecule of interest;
   identifying and grouping each conformer in the list of conformers based on the ranking of the calculated average electron density (AED) values for each conformer of the second molecule of interest;
   identifying any conformers of the second molecule of interest matching the identified at least one conformer of the target molecule of interest having the desired chemical, material, or pharmaceutical properties, said matching occurring for any conformers sharing calculated average electron density (AED) values within up to a 1.5% deviation from one another; and
   selecting the identified conformers of the second molecule of interest for further analysis,
   wherein the desired chemical, material, or pharmaceutical properties are one or more selected from the group consisting of pharmacokinetic and pharmacodynamic properties, potency, solubility, permeability, metabolic stability, transporter effects, bioavailability, metabolism, clearance, toxicity, specificity, reduced side effects, electron conductivity, malleability, color, resistance, degradability, and mechanical, electrical, thermal, magnetic, optical, or deteriorative properties which may impact surface chemistry.

2. The method of claim 1, further comprising synthesizing the identified conformers of the second molecule of interest to conduct the further analysis.

3. The method of claim 1, wherein the desired shape permits the identified conformers of the target molecule of interest and the second molecule of interest to bind to an active site of a receptor of interest.

4. The method of claim 1, wherein the conformers having the desired shape share similar material properties.

5. The method of claim 1, wherein the desired shape permits the identified conformers of the target molecule of interest and the second molecule of interest to react with other molecules.

6. The method of claim 1, wherein the further analysis comprises investigating the identified conformers of the target molecule of interest and the second molecule of interest for the desired chemical, material, or pharmaceutical properties.

7. The method of claim 1, wherein the identified conformers of the target molecule of interest and the second molecule of interest having the desired chemical, material, or pharmaceutical properties can be used for one or more activities selected from the group consisting of optimizing pharmaceutical properties, improving potency, enhancing specificity, reducing side effects, saving money in developing new drugs, speeding drug design processes, reducing patient pain, promoting the molecule's desired change in state, malleability, color, resistance, permeability, degradability, or breaking points, improving chemical processes, differentiating which catalyst is active or not; expediting reaction synthesis; optimizing chemical reactivities; selecting environmental molecules can be considered that are minimally polluting based on their interactions with a given receptor; improving human environmental conditions, improving the overall health of the Earth; identifying chemicals/drugs which should be banned for society's safety, determining toxicity; determining degree of harm to the environment, reducing use of costly experimental tests, select conformers suitable for use in aromatherapy or in perfumeries, and any combination thereof.

8. The method of claim 1, wherein the matching occurs for any conformers sharing calculated average electron density (AED) values within up to a 1% deviation from one another.

9. The method of claim 1, wherein the matching occurs for any conformers sharing calculated average electron density (AED) values within up to a 0.5% deviation from one another.

10. The method of claim 1, further comprising obtaining, via the AED tool, shapes of electrostatic potential (ESP) maps of the conformers of the second molecule of interest sharing similarities with shapes of ESP maps of the conformers of the target molecule of interest.

* * * * *